United States Patent [19]

Leaseburge et al.

[11] Patent Number: 4,487,080
[45] Date of Patent: Dec. 11, 1984

[54] SEAL FOR LIQUID INJECTION VALVE FOR GAS CHROMATOGRAPHY

[75] Inventors: Emory J. Leaseburge, Lewisburg; Curtis L. Perkins, Ronceverte, both of W. Va.

[73] Assignee: Combustion Engineering, Inc., Windsor, Conn.

[21] Appl. No.: 502,363

[22] Filed: Jun. 8, 1983

[51] Int. Cl.³ .............................................. G01N 1/20
[52] U.S. Cl. ............................. 73/863.83; 73/864.83; 277/162
[58] Field of Search .......... 73/863.71, 863.72, 863.73, 73/863.83, 863.85, 864.34, 864.81, 864.82, 864.83; 277/101, 157, 162, 163

[56] References Cited

U.S. PATENT DOCUMENTS

| 3,583,231 | 6/1971 | Felton | 73/863.83 |
| 3,612,545 | 10/1971 | Storms | 277/162 |
| 3,643,511 | 2/1972 | Warncke | 73/863.83 |
| 3,751,992 | 8/1973 | Morgan | 73/863.83 |

*Primary Examiner*—S. Clement Swisher
*Attorney, Agent, or Firm*—Troxell K. Snyder; Bruce L. Lamb

[57] ABSTRACT

A sampling valve having a stem which reciprocates between a liquid filled chamber and a vaporizing chamber is provided with a stem seal comprised by a thermoplastic bushing fitted to the valve stem with an interference fit. The bushing is encircled by a compression band exerting a radial compressive force and is mounted in the valve body with end clearance to avoid axial compression.

2 Claims, 4 Drawing Figures

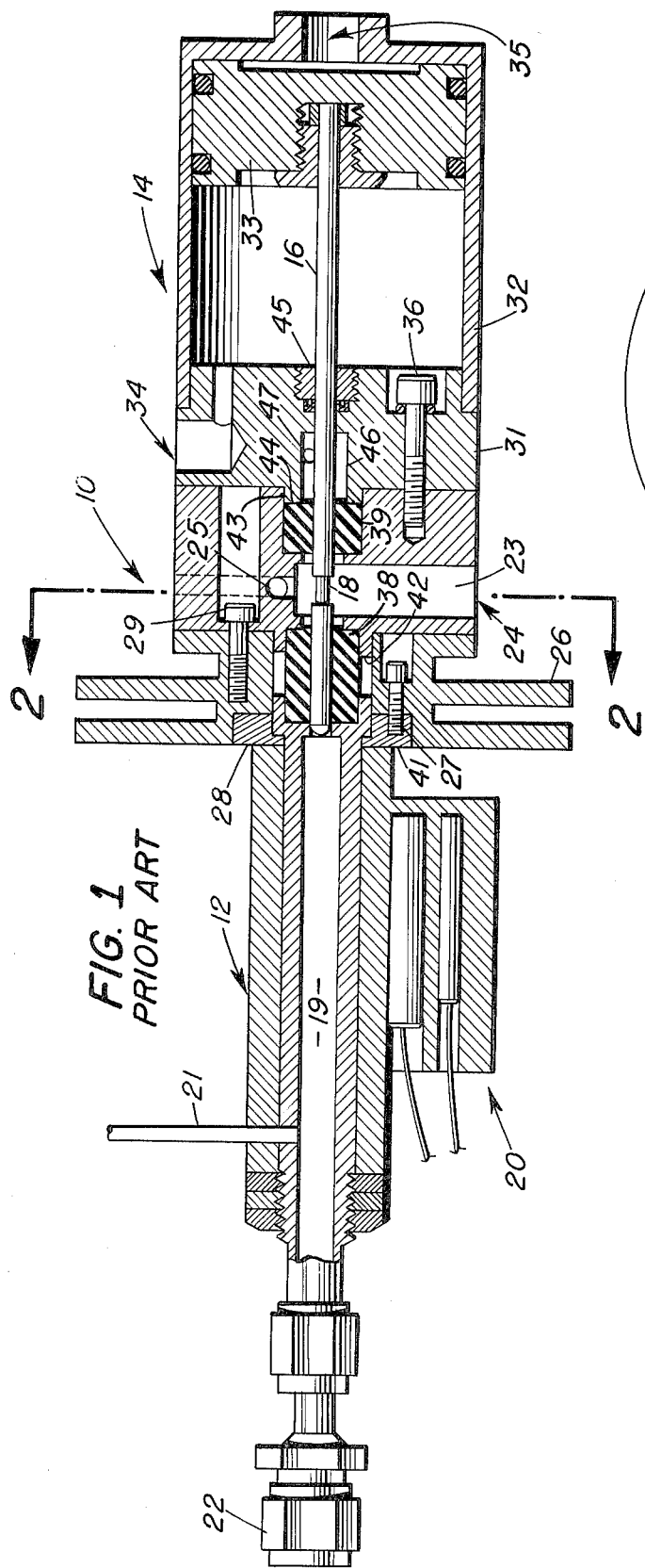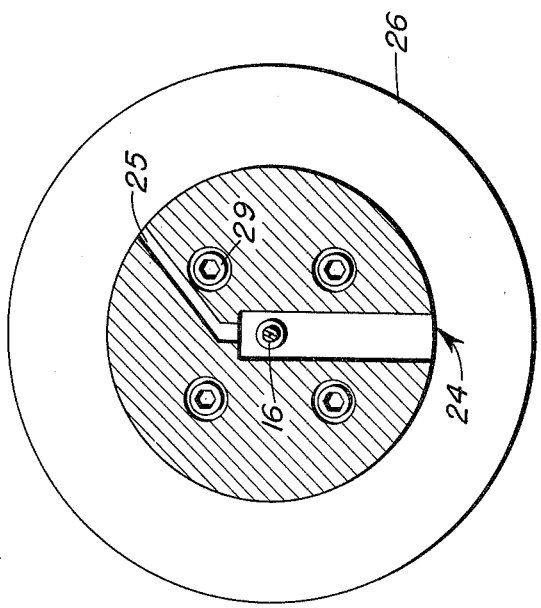
FIG. 1 PRIOR ART
FIG. 2

SEAL FOR LIQUID INJECTION VALVE FOR GAS CHROMATOGRAPHY

The present invention relates to liquid sampling valves for use with analytical apparatus. More particularly, it relates to improved sealing means for a liquid sampling valve stem which affords increased service life for the stem seal and increased accuracy of the volume of sample delivered by the valve to the analytical apparatus.

A gas chromatograph is a commonly used analyzer in chemical process controls. When the product stream is a liquid, means are required for extracting a sample of known volume from the stream, for rapidly vaporizing the sample and for injecting it into the separation column of the chromatograph. For this purpose, a liquid sampling valve has been developed which comprises a valve stem having a sample-carrying recess formed therein. The valve stem is caused to reciprocate between a valve chamber through which a portion of the product stream flows and a vaporizing chamber where the sample, trapped within the valve stem recess, is rapidly vaporized. The vaporized sample is swept into the separating column of the chromatograph by a carrier gas flowing through the vaporizer.

Conventionally, the valve stem is sealed in the valve body by cylindrical thermoplastic bushings positioned in the valve body at the points of entry of the valve stem into the liquid sample chamber. The seals operate under severe conditions of temperatures and pressure, causing distortion of the seals and necessitating frequent removal of the valves from service for replacement of the seals to prevent leakage and delivery of erroneously sized volumes to the analyzer.

It is an object of the present invention to provide sealing means for a reciprocating valve stem in a liquid sampling valve which will maintain dimensional stability in a relatively high temperature, high pressure operating environment whereby accurate sample volumes will be delivered by the valve during a substantially lengthened service life.

It is another object of the invention to provide sealing means for a reciprocating valve stem in a liquid sampling valve which requires less frequency replacement and which may be more readily serviced than the sealing means heretofore used in such valves.

Briefly, in accordance with the invention, the prior cylindrical bushing seal which was fitted to the valve stem with an interference fit and mounted in the valve body under an axial compression load is replaced by a cylindrical bushing banded by a spring collar to maintain the bushing under a uniform radial compression load through substantially the entire axial length of the bushing. The banded bushing is comparatively loosely mounted in the valve body with O-ring seals to prevent leakage from around the outer circumference of the banded bushing and to allow a certain amount of axial and radial play of the sealing means in the valve body, thereby reducing problems of obtaining and maintaining proper alignment between the valve stem and sealing means during assembly and operation.

In the drawings:

FIG. 1 is a pseudo-sectional view of a liquid sampling valve containing the stem sealing means of the prior art;

FIG. 2 is a sectional view taken along the line 2—2 of FIG. 1;

Figure 3:
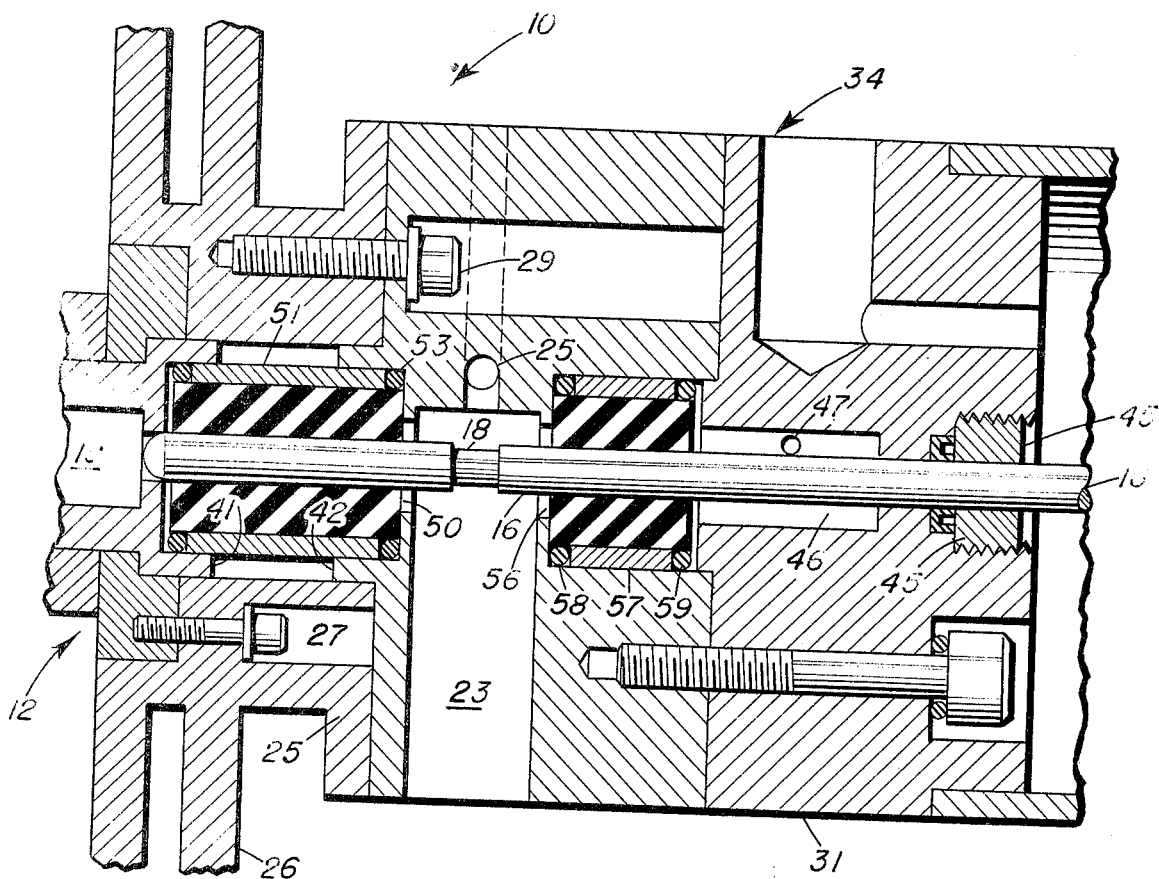
FIG. 3 is an enlarged sectional view of the improved sealing means of the invention.

FIG. 1 shows a liquid sampling valve of the prior art used to furnish accurately measured volumes of a liquid sample to a gas chromatograph analyzer. The major elements of the valve comprise a valve body 10, a vaporizer 12 and a pneumatic actuator 14. A valve stem 16, having a sample-carrying recess 18 formed therein, is reciprocated by the actuator 14 between the retracted position shown and a forward position wherein recess 18 and the liquid trapped therein is carried into the evaporating chamber 19 of vaporizer 12. Chamber 19 is maintained at high temperature by an electrical heater 20 so as to cause the liquid sample carried therein to flash rapidly into vapor. The sample vapors are swept, preferably as a "plug" of undiluted vapor, from chamber 19 to the inlet of the analyzer separating column by an inert carrier gas which enters the evaporating chamber through tube 21. The analyzer separating column (not shown) is connected to chamber 19 at fitting 22.

Liquid to be sampled flows under pressure through chamber 23, entering at port 24 and exiting through vent 25. Chamber 23 is thus maintained filled with pressurized liquid at all times.

Also referring to FIG. 2, valve body 10 is coupled to vaporizer 12 through a thermal isolator 25 formed with heat dissipating fins 26. A pair of diagonally positioned cap screws 27 recessed in isolator 25 secure vaporizer 12 to isolator 25 by engagement with a flanged collar 28 which bears on a base shoulder of chamber 19. Valve body 10 is secured to isolator 25 by four cap screws 29 recessed in the body and spaced to clear screws 27.

Actuator 14 comprises a base 31 with a cylinder 32 threaded thereon. A piston 33 secured to valve stem 16 operates in cylinder 32 under the action of compressed air admitted through ports 34 or 35, depending on the desired direction of motion of the piston. Actuator 14 is secured to valve body 10 by four circumferentially spaced cap screws 36 recessed on base 31.

Valve stem 16 is sealed in valve body 10 by cylindrical bushings 38 and 39 formed of a thermoplastic material such as polytetrafluoroethylene (teflon). Bushing 38 is retained between dish-like seats 41 and 42, respectively, formed in the base of evaporating chamber 19 and in valve body 10. The facing edges of the lips of seats 41 and 42 are spaced apart so that when valve body 10, thermal isolator 25 and vaporizer 12 are assembled, bushing 38 will be axially compressed. Bushing 39 fits within a bore 43 in valve body 10. An upstanding lip 44 on actuator base 31 fits within bore 43 and bears on bushing 39 so as to compress the bushing axially when actuator 14 is assembled to valve body 10. Valve stem 16 is sealed in base 31 by a packing gland 45. A counter bore 46 in cylinder base 31 adjacent bushing 39, vented to the outside of the actuator through opening 47, permits escape of any liquid leaking past bushing 39 to prevent seepage of liquid into the actuator.

As will be apparent from the construction of the valve, delivery of accurately sized sample volumes from the chamber 23 to the vaporizer 19 is dependent upon close conformity of the interior bore of bushing 38 to the surface at the major diameter of valve stem 16 throughout the length of travel of the valve stem through the bushing. A separation between the bushing inner surface and the valve stem surface creates a void into which some of the liquid retained by recess 18 will spill with the result that the intended volume of sample will not be delivered by the valve to the vaporizer. In practice, it has been found that the tendency of the thermoplastic bushing material to creep under high temperature and pressure causes dimensional changes requiring replacement of such prior art bushings even before any leakage of liquid is observed.

Figure 4:
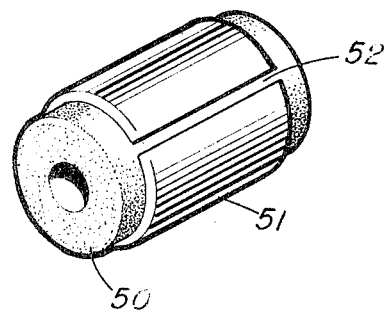
FIG. 4 is a perspective view of the bushing-collar assembly of the invention.

The improved valve stem seal of the invention is shown in FIG. 3 which is an enlarged partial sectional view of the valve stem seal area. Bushing 38 is replaced by a bushing 50 of similar thermoplastic material also fitted to valve stem 16 with an interference fit. The length of bushing 50 is shortened from that of bushing 39 so that when valve body 10, thermal isolator 25 and vaporizer 12 are assembled an end clearance exists between bushing 50 and seats 41 and 42. As best seen in FIG. 4, bushing 50 is banded along substantially the entire length by a split collar 51. Collar 51 is fashioned from a complete ring having an inside diameter smaller than the outside diameter of bushing 50. The collar is split at 52 and expanded to permit insertion of bushing 50. After assembly of collar and bushing, the spring force of the collar maintains the bushing under uniform radial compression substantially through its entire length. The outside dimension of collar 51 is sized so that after assembly with bushing 50 the assembly will fit into seats 41 and 42 with a slight clearance. O-rings 52, 53 installed over the ends of bushing 50 protruding beyond collar 51, prevent leakage of liquid from chamber 23 along the outside of collar 51 into chamber 19.

Rear bushing 39 of FIG. 1 is replaced by a seal comprising a bushing 56 of thermoplastic, split collar 57 and O-rings 58, 59. Similarly to bushing 50, the bore of bushing 56 is sized for an interference fit with valve stem 16. Collar 57, like collar 51, is split and is dimensioned to exert uniform radial compression upon bushing 56 substantially along its entire length. The outside dimension of collar 57 and the length of bushing 56 are chosen so that the bushing and collar assembly fits within bore 43 with slight side and end clearances. O-rings 58 and 59 prevent leakage of liquid from chamber 23 along the outside of collar 57.

The invention claimed is:

1. In a liquid sampling valve for use with a gas chromatograph analyzer, said valve including a valve body, a chamber within said valve body for containing a liquid to be sampled, a heated vaporizing chamber adjacent said valve body, a valve stem having a sample-carrying recess therein and means for reciprocating said valve stem between a position wherein said valve stem recess is located in said valve body chamber for immersion in the liquid contained therein and a position wherein said valve stem recess is located in said vaporizing chamber, a liquid sample of specific volume being transported from said valve body chamber to said vaporizing chamber by said reciprocation, improved valve stem sealing means for preventing leakage of liquid from said valve body chamber without loss of liquid sample volume during reciprocation of said valve stem, comprising, a cylindrical bushing of thermoplastic material having a central bore for receiving said valve stem, said central bore being sized to provide an interference fit between said bushing and said valve stem;

a split circular collar of resilient metal, said collar having an inside diameter smaller than the outside diameter of said bushing when fabricated, said collar encircling said bushing substantially along the entire length of said bushing and maintaining said bushing under uniform radial compression substantially along the entire length thereof;

means for mounting said bushing and collar in a position separating said valve liquid chamber and said vaporizing chamber to permit reciprocating motion of said valve stem between said liquid chamber and said vaporizing chamber, said mounting means being dimensioned to provide end and side clearance space for said bushing and said collar; and sealing means at the opposite ends of said bushing respectively abutting said valve body and said vaporizing chamber.

2. The improved seal of claim 1 wherein said bushing end sealing means comprises a pair of O-rings, one each being positioned at each end of said bushing.

* * * * *